United States Patent
Nichols

(10) Patent No.: US 6,884,998 B2
(45) Date of Patent: Apr. 26, 2005

(54) METHOD AND APPARATUS FOR DETERMINING ELECTRICAL CONTACT WEAR

(75) Inventor: Bruce Nichols, Dallas, TX (US)

(73) Assignee: Nichols Applied Technology, LLC

( * ) Notice: Subject to any disclaimer, the term of this patent is extended or adjusted under 35 U.S.C. 154(b) by 0 days.

(21) Appl. No.: 10/318,859

(22) Filed: Dec. 13, 2002

(65) Prior Publication Data

US 2004/0113070 A1 Jun. 17, 2004

(51) Int. Cl.$^7$ .................................................. G01T 1/161
(52) U.S. Cl. .................. 250/302; 250/461.1; 250/484.2
(58) Field of Search ................................ 250/259, 260, 250/302, 461.1, 484.2

(56) References Cited

U.S. PATENT DOCUMENTS

| | | | | | |
|---|---|---|---|---|---|
| 4,532,499 | A | * | 7/1985 | Collin et al. ................. | 340/644 |
| 4,929,837 | A | * | 5/1990 | DiVita et al. ............. | 250/461.1 |
| 5,200,615 | A | * | 4/1993 | Hopenfeld ................... | 250/302 |
| 5,453,591 | A | * | 9/1995 | Stroud .......................... | 218/43 |
| 5,941,370 | A | * | 8/1999 | Nichols ....................... | 200/262 |
| 6,023,036 | A | * | 2/2000 | Nichols ....................... | 218/91 |
| 6,231,227 | B1 | * | 5/2001 | Andersen ....................... | 374/4 |
| 6,361,205 | B1 | * | 3/2002 | Andersen ...................... | 374/45 |
| 6,466,023 | B1 | * | 10/2002 | Dougherty et al. ......... | 324/424 |
| 2003/0071212 | A1 | * | 4/2003 | Weiland et al. ............. | 250/302 |

* cited by examiner

*Primary Examiner*—David Porta
*Assistant Examiner*—Davienne Monbleau
(74) *Attorney, Agent, or Firm*—Sanford E. Warren, Jr.; Winstead Sechrest & Minick P.C.

(57) ABSTRACT

A fluorescent trace material is provided within at least a portion of an electrical contact or interrupter assembly component, or a cavity defined therein. At least a portion of the fluorescent trace material is exposed or released from the electrical contact or interrupter assembly component, indicating a degree of component wear.

4 Claims, 5 Drawing Sheets

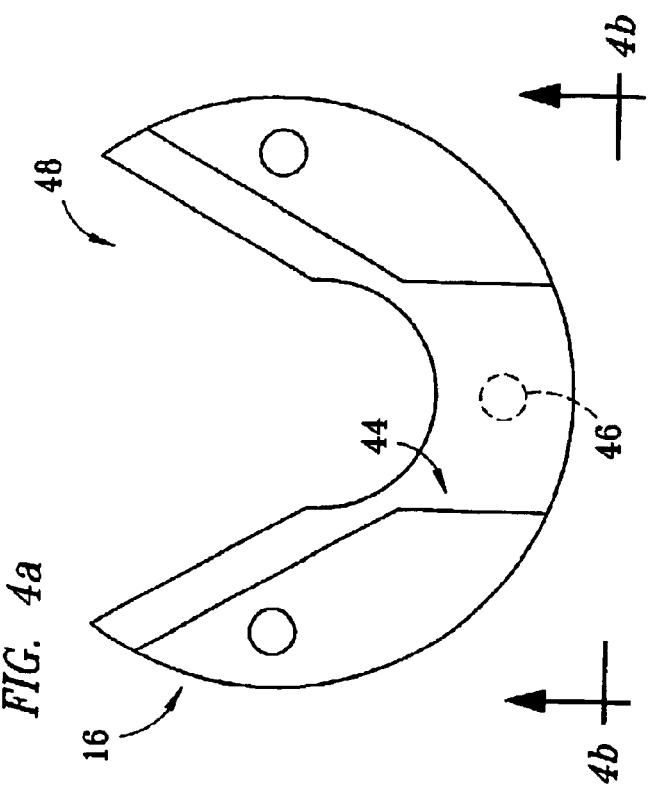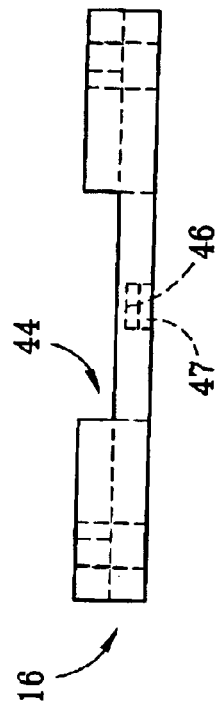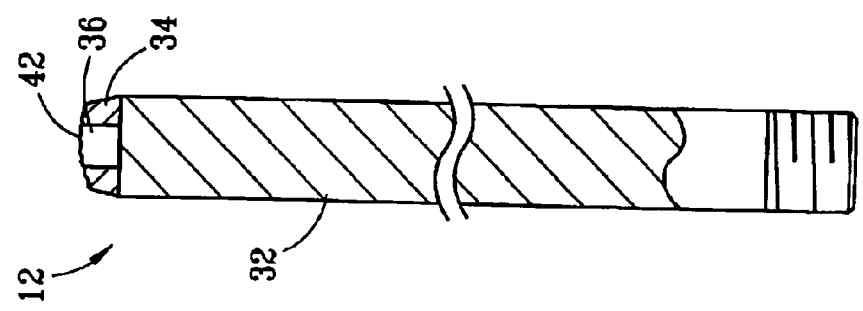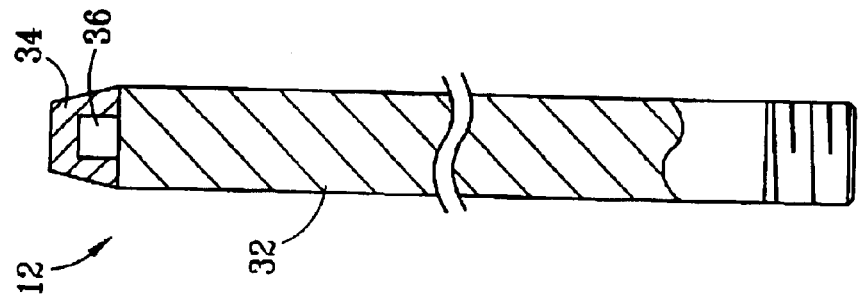

METHOD AND APPARATUS FOR DETERMINING ELECTRICAL CONTACT WEAR

FIELD OF THE INVENTION

The present invention relates in general to electrical switches and in particular to detecting the extent of erosion or wear of electrical contacts and interrupter assembly components caused by arcing or mechanical wear.

BACKGROUND

A variety of electrical equipment contain switches which interrupt or direct the path of electricity through an electric circuit. Circuit breakers, for example, are switches used to open a circuit in the event of a fault, or short circuit. Another type of switch is a load tap changer, which is used to automatically select a particular tap corresponding to a connection within the secondary windings of a transformer.

The parts of a switch which actually perform the function of connecting and disconnecting the current path are called contacts. In high voltage equipment, the contacts of electrical switches operating under load generally erode over time during operation. The erosion of electrical contacts most commonly results from the arcing that occurs whenever a switch breaks, or interrupts, a circuit. An arc is formed as the electrical contacts move apart from or toward each other and the electric potential between them causes electrons to bridge the inter-contact space region. A current is maintained in the arc until the spacing between the contacts, and thus the impedance, increases enough to prevent electrons from bridging the gap for the given voltage potential, or, if moving toward each other, until the contacts are touching. The current flowing across the gap generates extreme heat, resulting in temperatures high enough to burn away some of the contact material.

Erosion of the contacts can cause failures or deteriorated switch operation and otherwise generally reduce or limit the useful lives of the switches themselves. Switches may fail when their contacts have eroded to such a degree that they cannot effectively complete a circuit, or when the erosion has changed the physical shape of the contact such that the mechanical operation of the switch is interrupted. Once a contact has eroded to the point at which further use risks injury to personnel or machinery, known as the "critical point," a contact's useful life is over.

Because arcing and erosion cannot be eliminated, switches are almost always designed to allow replacement of the contacts. It is typically less expensive to replace worn contacts than to replace an entire switch when the contacts have eroded to the critical point or close thereto. As a result, users of switches must monitor the erosion of the contacts to recognize when the predetermined critical point is approaching or has been reached. Replacing worn contacts at or before the critical point is important because contacts used past that point continue to erode and may cause the switch to fail. A switch failure can have a negative or catastrophic effect on equipment and presents a danger to personnel. On the other hand, replacing contacts before the end of their useful life increases material and labor costs.

There is a large expense associated with electrically isolating, or de-energizing, and physically inspecting high voltage electrical equipment to determine the extent of wear or erosion of the contacts. This expense is compounded by the necessity of removing, storing, and processing a large quantity of oil, sometimes up to 1000 gallons. Contacts are often replaced early due to the difficulty of predicting the rate of erosion from one maintenance cycle to the next. The expense of inspecting the contacts is often so great that many times maintenance departments change some of the contacts during every inspection, even though the contacts may have months or more of useful life remaining. Properly matching the timing of inspection with the end of the useful life of the contacts would thus advantageously result in a cost savings.

One means commonly used to monitor electrical equipment performance and identify equipment requiring maintenance is the use of dissolved gas analysis (DGA). In DGA, a sample of the oil surrounding the contacts is extracted and analyzed to monitor for dissolved gases. The presence of certain gases is indicative of various types of problems that may be occurring within the equipment. For example, the presence of acetylene dissolved in the oil surroundings can be indicative of excessive heating within load tap changers and transformers. The DGA method of monitoring, however, lacks the precision necessary to determine the proper timing of contact replacement, as the presence of dissolved gases related to erosion has no correlation to the amount or extent of erosion of the contacts.

There is accordingly a need to provide a method and apparatus for the detection of the extent of electrical contact erosion, or wearing, that is inexpensive and may be used on-site as well as in the laboratory.

SUMMARY OF THE INVENTION

The invention relates to an improved sacrificial electrical contact or interrupter assembly component. At least a portion of the electrical contact or interrupter assembly component, or a cavity defined therein, comprises a fluorescent trace material. At least a portion of the fluorescent trace material is exposed or released, indicating a degree of component wear.

In one aspect of the invention, a method and apparatus are provided for detecting the exposed or released trace material.

In another aspect of the invention, the presence or quantity of trace material is monitored as an indication of contact wear.

In yet another aspect of the invention, a trace material is provided within a baffle plate in an interrupter assembly.

BRIEF DESCRIPTION OF THE DRAWINGS

For a more complete understanding of the present invention and the advantages thereof, reference is now made to the following description taken in conjunction with the accompanying drawings, in which:

FIG. 3a is a partial section of a contact assembly containing an erosion indicator;

FIG. 3b is a partial section of a contact assembly that has suffered erosion due to arcing;

FIG. 4a is a top view of a baffle plate;

FIG. 4b is a side view of a baffle plate, taken along line 4b—4b of FIG. 4a;

FIG. 11b is a top view, in partial section, of the remote optical access port of FIG. 11a, taken along line 11b—11b of FIG. 11a.

DETAILED DESCRIPTION

Figure 1:
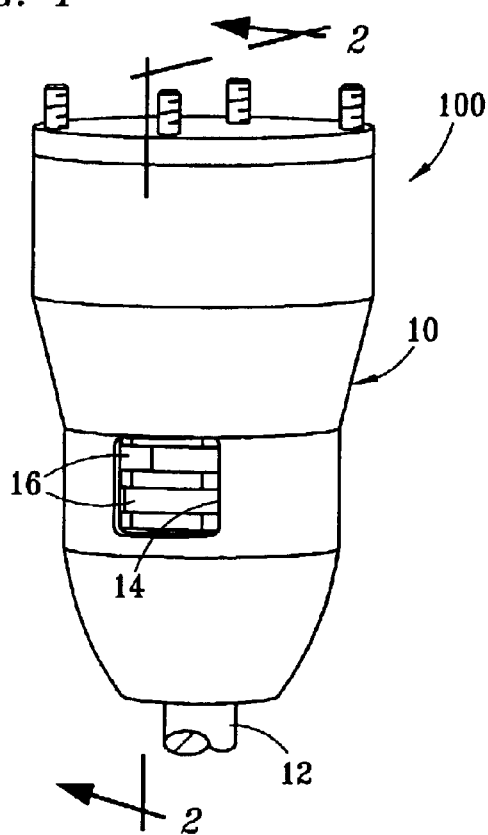
FIG. 1 is a perspective view of an interrupter assembly that may be used within a typical circuit breaker.

FIG. 1 shows an interrupter assembly 100 that may be used as part of a circuit breaker (not shown), for example. Interrupter assemblies generally are well-known in the art. The interrupter assembly 100 includes an interrupter shell 10 surrounding a male contact assembly 12 and a female contact assembly (not visible in FIG. 1). The interrupter shell 10 is preferably fabricated from a strong, non-conducting material such as phenolic cellulose tubing or fiberglass. The shell 10 wall is of sufficient thickness to contain the arc and to withstand the forces created by the arc-gas expansion during arcing. The interrupter assembly 10 is generally housed in an enclosure such as a tank or switch compartment, and surrounded by an insulating, non-conductive medium that may comprise oil, air, or inert gas. Also shown in FIG. 1 is an exhaust port 14 and an assembly of baffle plates 16.

Figure 2:
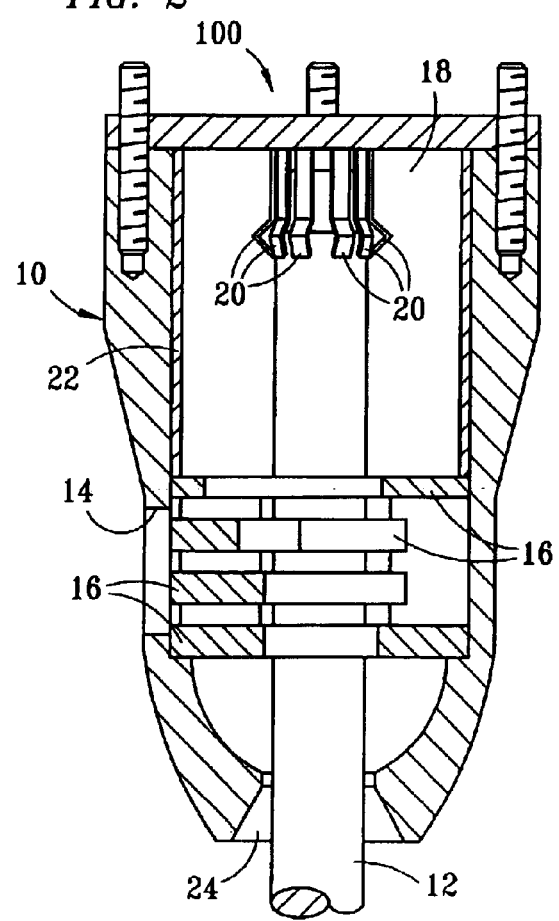
FIG. 2 is a section, taken along line 2—2 of FIG. 1, illustrating the position and arrangement of typical contact assemblies within the interrupter assembly.

In FIG. 2, a female contact assembly 18 is shown within the interrupter shell 10. The female contact assembly 18 comprises a plurality of contact segments 20, which are preferably arranged in a circular pattern. The contact segments 20 are preferably configured to engage the male contact assembly 12 and are preferably biased toward the male contact assembly 12 to promote electrical contact therewith.

The baffle plates 16 can be seen more clearly in FIG. 2. Four (4) baffle plates 16 are shown in this embodiment, although a greater or smaller number may be used. The baffle plates 16 are held in place by a spacer 22, which is a cylindrical tube, preferably made of non-conducting fiber such as phenolic cellulose tubing, which slides into the interrupter shell 10. The baffle plates 16 are described in more detail below, in connection with FIGS. 4a and 4b.

Under normal conditions, the end of the contact assembly 12 extends into the interrupter assembly 100 via the opening 24 at the base of the interrupter assembly shell 10. During operation, the contact assembly 12 extends through the baffles 16, and penetrates into, or engages, the female contact assembly 18, allowing electric current to flow through the assembly. The contacts within the interrupter assembly are designed to open upon the occurrence of certain events, such as a fault, or short circuit, or a manual switch (not shown) being tripped. When the circuit breaker is tripped, the contact assembly 12 is rapidly retracted away from the female contact assembly 18 and from the interrupter shell 10. As the contact assembly 12 is pulled away from the female contact assembly 18, an arc will typically occur between the contacts.

FIGS. 3a and 3b show the contact assembly 12 in more detail. The contact assembly 12 comprises a base 32 and a contact tip 34. The base 32 is preferably constructed from copper, although any electrically conductive material may be used. The contact tip 34 is preferably constructed from a material resistant to erosion from arcing, preferably a tungsten-based alloy. The contact assembly 12 comprises one or more cavities 36, preferably defined in the contact tip 34, but which may alternatively be located elsewhere in the contact assembly 12, provided at least a portion of the cavity 36 is subject to exposure to the surrounding medium (not shown) as a result of erosion due to arcing. A trace material (not shown) is provided in the cavity 36. The contact tip 34 is then preferably brazed onto the base 32 so that the trace material is sealed within the cavity 36.

As the interrupter assembly 100 is used, the contact tip 34 erodes due to arcing. When the contact tip 34 has eroded to the level of the cavity 36, an opening 42 to the cavity is created, as shown in FIG. 3b. The trace material is then in contact with the surrounding medium, and at least a portion of the trace material is released from the cavity 36 into the surrounding medium. The surrounding medium is monitored for the presence of the trace material, the presence of which indicates that the contact assembly 12 requires replacement.

Alternatively to providing the fluorescent trace material in one or more cavities, the material may, instead, be distributed within the material comprising the contact assembly 12, the contact tip 34, the base 32, or any portion of these components. In that case, the fluorescent trace material is released into the surrounding medium more gradually as the contact assembly 12, or applicable portion thereof, erodes. At least one point in the surrounding medium is then monitored until a sufficient quantity of trace material is detected to indicate that the contact assembly 12 should be replaced.

The trace material preferably comprises at least one fluorescent trace material. Fluorescent trace material refers to any material that emits electromagnetic radiation when stimulated by the absorption of incident electromagnetic radiation, whether by fluorescence, phosphorescence or other wave-length specific process. The fluorescent component emits electromagnetic radiation when it is "excited," that is, when it is exposed to incident electromagnetic radiation within a particular frequency range. The molecules comprising the fluorescent component absorb the incident electromagnetic radiation and then emit electromagnetic radiation, preferably of a different wave-length than that absorbed. Preferably, a fluorescent component is chosen with an excitation wave-length in the ultraviolet range and which emits visible light upon excitation. Choosing a fluorescent component with excitation and emission frequencies within these ranges makes detection simpler, because the electromagnetic radiation emitted by the fluorescent component may be readily distinguished from reflected electromagnetic radiation used for exciting the fluorescent component.

Additionally, components comprising the trace material should preferably be able to withstand the high temperatures involved in the brazing process, typically between 1000 and 1250 degrees Fahrenheit. Generally, this means inorganic materials should be chosen.

Most preferably, the trace material comprises refined tungsten ore, or calcium tungstate ($CaWO_4$). Calcium tungstate fluoresces when exposed to incident electromagnetic radiation with a wave-length of about 254 nm, in the short wave-length ultraviolet range, and emits visible light. Calcium tungstate has a high temperature resistance and is relatively inexpensive and readily available, compared to other fluorescent materials. Further, because tungsten is widely used in electrical switches, the use of calcium tungstate in the fluorescent trace material does not represent an introduction of any foreign metallic constituent into the high voltage equipment, thus alleviating potential customer concerns. Nevertheless, other fluorescent materials are known, many of which could be used in the trace material.

FIGS. 4a and 4b illustrate one configuration of a baffle plate 16 that may be used in an interrupter assembly 100. The baffle plate 16 controls the flow of gases produced as a result of arcing ("arc-gases")(not shown) through the arc-gas exhaust port 14 and aids in constricting the arc (not shown) and directing the arc into the exhaust port 14. The arc and arc gases are directed through a reduced section channel 44 defined in the baffle plate 16, which is directed toward the exhaust port 14. The exhaust port 14 is directed toward an arc barrier chamber, which prevents the arc and arc-gasses from contacting the tank, or switch compartment, or other nearby components within the equipment. There is preferably either a notch 48 or a hole (not shown) defined in each baffle plate 16, which allows the contact assembly 12 to extend through the baffle plates 16.

The baffle plates 16 are preferably constructed from a non-conductive material with sufficient strength to withstand the high forces created by arcing. Additionally, the baffle plates 16 are preferably constructed from a material that will at least partially vaporize when exposed to arcing. The reason is so that any material which is released from the baffle plates 16 as a result of arcing will be vaporized, rather than remain as particulate debris within the surrounding medium. Preferably, the baffle plates 16 are constructed from melamine-fiber reinforced melamine resin. However, many other materials which may be used to construct the baffle plates 16 are known in the art and may be used in the present invention.

Because of the tendency of baffle plates 16 used in an interrupter assembly 100 to experience wear over time as a result of arcing, it is necessary to replace the baffle plates 16 before they become so worn that the baffle plates 16 no longer function effectively. So that the optimal replacement time may be conveniently determined without necessitating disassembling the interrupter assembly 100 for visual inspection, it is preferable to use a trace material in the baffle plates 16, similarly to the use described above in connection with the contact assembly 12.

As shown in FIG. 4a, a cavity 46 is defined in the baffle plate 16, preferably near the channel 44 and the exhaust port 14. The cavity 46 is preferably created by machining a shallow depression in the underside of the baffle plate 16. A trace material (not shown) is provided in the cavity 46. The trace material is preferably a fluorescent trace material, although other trace materials may alternatively be used. A cover 47 is preferably provided to seal the cavity 46. The cover 47 preferably comprises a thin layer of the same material as that used for construction of the baffle plates 16. As the baffle plates 16 experience wear as a result of arcing, eventually an opening (not shown) to the cavity 46 will develop, allowing at least a portion of the trace material to escape into the surrounding medium. The surrounding medium is monitored for the trace material, the presence of which indicates at least one baffle plate 16 is in need of replacement.

Alternatively to providing the trace material in one or more cavities, the material may, instead, be distributed within the material comprising the baffle plate 16, or any portion of thereof. In such case, the trace material is released into the surrounding medium gradually as the baffle plate 16, or applicable portion thereof, erodes. At least one point in the surrounding medium is then monitored until a sufficient quantity of trace material is detected to indicate that at least one baffle plate requires replacement.

The trace material may comprise the same material used as a trace material in connection with the contact assembly 12. Alternatively, a different trace material may be selected so that, by identifying which trace material is present in the surround medium, the user may identify whether the contact assembly 12 or baffle plates 16 require replacement. Further, a non-fluorescent trace material may be used, provided an appropriate detection means is also used.

Figure 5:
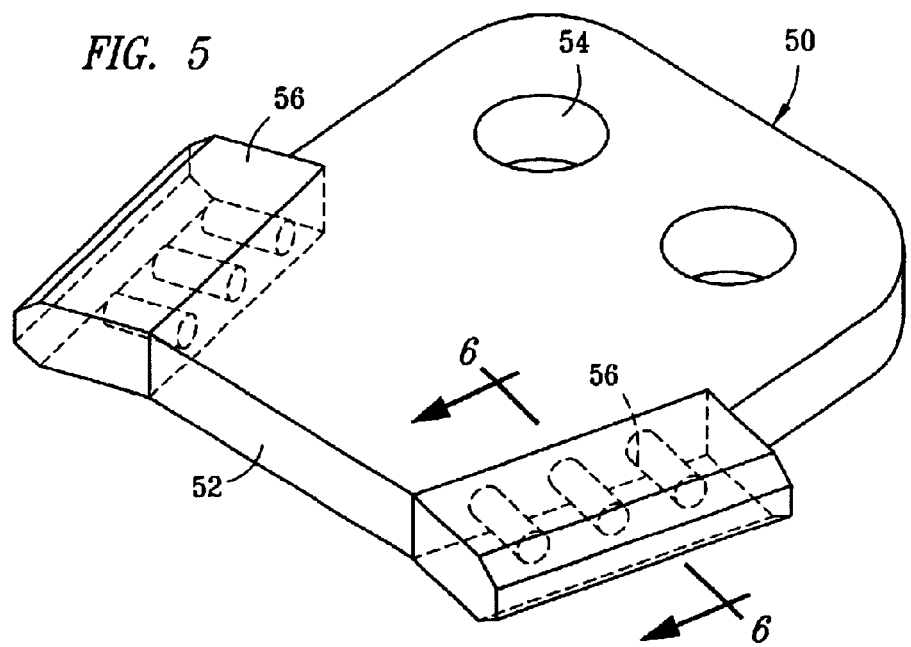
FIG. 5 is a perspective view of a contact assembly containing an erosion indicator.

Shown in FIG. 5 is another embodiment of a contact assembly 50 including an erosion indicator. Contact assembly 50 is of the type that may be used in a load tap changer selector switch that does not transfer or divert current during tap changing operations and therefore experiences arcing during the normal operation of a transformer (not shown). In a selector switch, one or more stationary contact assemblies 50 are provided for each of the taps of a secondary winding (not shown) in a transformer. A second part of the selector switch, the moving contact assembly (not shown), is used to conductively engage the contact assembly 50, thereby allowing selection of the secondary winding tap chosen by the user. The selector switch, of which the contact assembly 50 is a part, switches between taps while under load, causing arcing and erosion.

The contact assembly 50 includes a base 52 preferably made of copper, although any electrically conductive material may be used. The base 52 may be provided with one or more holes 54 for mounting to a selector switch. One or more contact tips 56 are bonded to and in electrical communication with base 54. The contact tips 56 are preferably made from a material that is conductive and resistant to erosion from arcing, such as a tungsten-based alloy. The contact tips 56 are preferably bonded to the base 52 by brazing.

Figure 6:
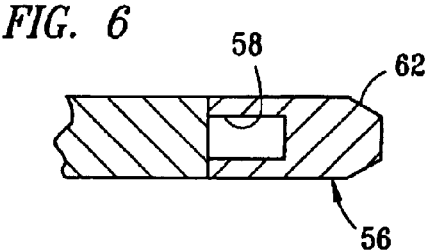
FIG. 6 is a partial section view, taken along line 6—6 of FIG. 5, showing the construction and assembly of the erosion indicator in greater detail.

The contact tips 56 are provided with one or more cavities 58. Cavities 58 are formed in the contact tips 56, such that the cavities 58 are sealed when the contact tips 56 are bonded to the base 52. After a cavity 58 is provided, a trace material (not shown) is inserted into the cavity 58, and the contact tip 56 is bonded to the base 52. The trace material is preferably as described above in connection with FIGS. 3a and 3b. Referring to FIG. 6, a contact tip 56 is shown as a partial section view along line 6—6 of FIG. 5. A partial representation of the base 52 is also shown. The contact tip 56 has a front edge 62, which is preferably beveled. Front edge 62 is the first part of the contact tip 56 to touch the second part of the selector switch when the switch closes, and it is the last part of contact tip 56 to separate from the opposite contact when the switch opens. Therefore, the front edge 62 is the surface of the contact tip 56 which is most subject to erosion from arcing.

As the contact assembly 50 is used, the contact tips 56 erode from arcing. When the contact tips 56 have eroded to a sufficient degree, the cavities 58 are opened. As a cavity 58 is opened, the trace material comes into communication with and is dispersed into the surrounding medium. When the presence of the trace material is detected in the surrounding medium, replacement of the contact assembly 50 is required.

Alternatively to providing the fluorescent trace material in one or more cavities, the material may, instead, be distributed within the material comprising the contact assembly 50, the contact tip 56, the base 52, or any portion of these components. In such case, the fluorescent trace material is released into the surrounding medium more gradually as the contact assembly 50, or applicable portion thereof, erodes. At least one point in the surrounding medium is then monitored until a sufficient quantity of trace material is detected to indicate that the contact assembly 50 should be replaced.

Figure 7:
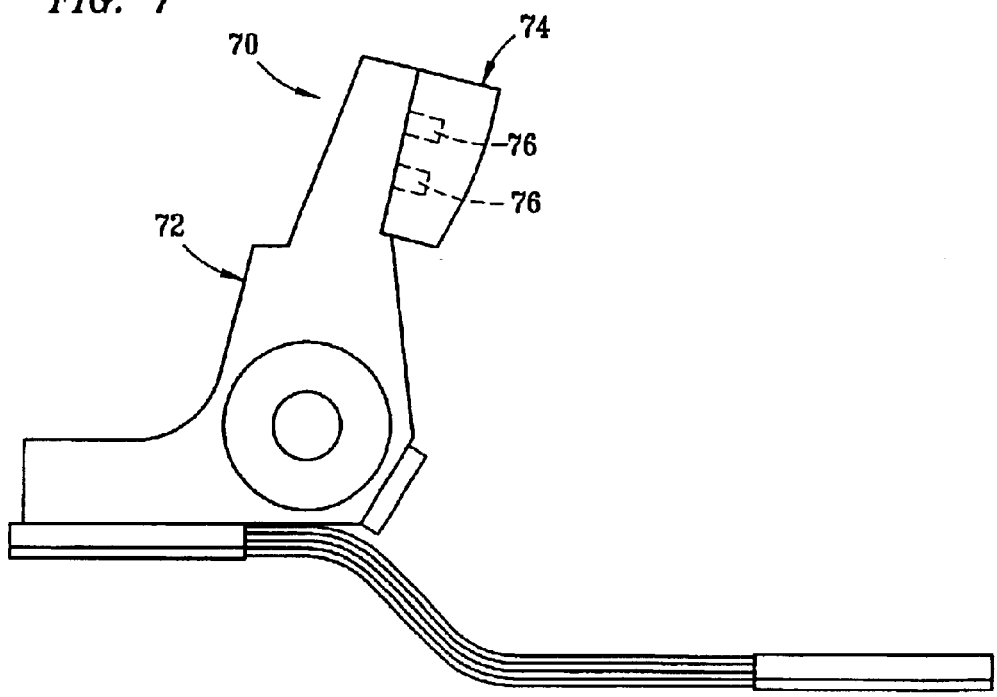
FIG. 7 is a side view of a transfer switch sacrificial contact assembly containing an erosion indicator.

Turning now to FIG. 7, another embodiment of a sacrificial contact is shown. Contact assembly 70 is used in a high voltage load tap changer to transfer, or divert, the electrical current prior to movement of the selector switch, and is accordingly subject to accelerated arcing and erosion as it operates during each operation of the selector switch. Contact assembly 70 comprises a base 72 and a contact tip 74. The contact tip 74 is provided with one or more cavities 76. A fluorescent trace material (not shown) is inserted into the cavities 76, and the cavities are sealed when the contact tip 74 is brazed to the base 72. The trace material is preferably as described above in connection with FIGS. 3a and 3b.

As the contact assembly 70 is used to create and break electrical circuits, erosion occurs. When the contact tip 74 is eroded to a sufficient degree, the cavities 76 are opened. As the cavities 76 are opened, the trace material comes into communication with and is dispersed into the surrounding medium. When the presence of the trace material is detected in the surrounding medium, replacement of the contact assembly 70 is indicated.

Alternatively to providing the fluorescent trace material in one or more cavities, the material may, instead, be distributed within the material comprising the contact assembly 70, the contact tip 74, the base 72, or any portion of these components. In that case, the fluorescent trace material is released into the surrounding medium more gradually as the contact assembly 70, or applicable portion thereof, erodes. At least one point in the surrounding medium is then monitored until a sufficient quantity of trace material is detected to indicate that the contact assembly 70 should be replaced.

Figure 8:
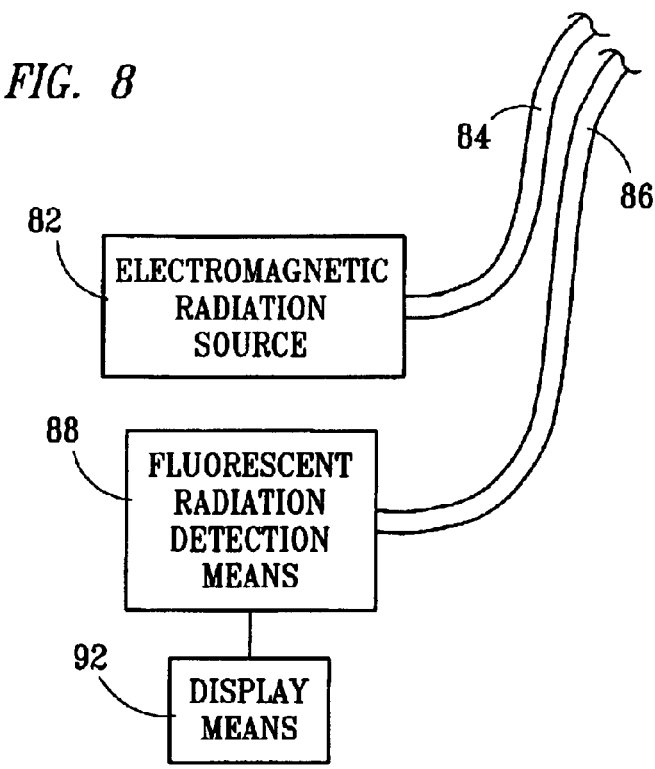
FIG. 8 is a schematic diagram of a fluorescent trace material monitoring or detecting system.

FIG. 8 is a schematic representation of a means for detecting a fluorescent material in a medium surrounding a contact assembly ("surrounding medium"). The detection means comprises an electromagnetic radiation source 82. The electromagnetic radiation source 82 generates electromagnetic radiation that is directed into the surrounding medium and used to excite any fluorescent trace material present in the surrounding medium. The electromagnetic radiation source 82 preferably generates electromagnetic radiation of a wave-length that is known to cause fluorescence in the particular fluorescent trace material being detected. As described above, such wave-length is preferably in the short wave-length ultraviolet light range, however electromagnetic radiation of other frequencies may also be used.

Many sources of ultraviolet light are known and may be used as the electromagnetic radiation source 82. Examples include fluorescent lamps, incandescent lamps and xenon lamps. The electromagnetic radiation from the electromagnetic radiation source 82 is directed to the surrounding medium using an electromagnetic radiation transmission means 84. The electromagnetic radiation transmission means 84 preferably comprises an optically-transmissive conduit, such as a fiber optic cable. Alternatively, the electromagnetic radiation transmission means 84 may comprise a transparent or translucent window or lens (not shown). In another embodiment, the electromagnetic radiation source 82 may be installed in the equipment tank (not shown) or switch compartment (not shown) within which the contact assembly is located so that a separate electromagnetic radiation transmission means 84 is unnecessary. In yet another embodiment, a sample of the surrounding medium is removed from the contact assembly housing and analyzed using an electromagnetic radiation source 82 in a laboratory environment.

Any fluorescent material present in the surrounding medium will emit its own electromagnetic radiation ("fluorescent radiation") in response to the electromagnetic radiation directed into the surrounding medium. Fluorescent radiation refers to electromagnetic radiation of any frequency that is produced in response to absorption of electromagnetic radiation, including by fluorescence, phosphorescence, or other wave-length specific process The fluorescent radiation is directed via a fluorescent radiation transmission means 86 to a fluorescent radiation detection means 88. The fluorescent radiation transmission means 86 preferably comprises an optically-transmissive conduit, such as a fiber optic cable. Alternatively, the fluorescent radiation transmission means 86 may comprise a transparent or translucent window or lens (not shown). The fluorescent radiation transmission means 86 may comprise the same structure or a different structure as the fluorescent radiation transmission means 86. Most preferably, the fluorescent radiation transmission means 86 and the electromagnetic radiation transmission means 84 comprise a single optical fiber. Alternatively, the fluorescent radiation detection means 88 may be installed within the tank or switch compartment within which the contact assembly is located so that a fluorescent radiation transmission means 86 is unnecessary. Additionally, a sample of the surrounding medium may be removed from the contact assembly tank or switch compartment and analyzed using a fluorescent radiation detection means 88 in a laboratory environment.

The fluorescent radiation detection means 88 may comprise any means that is useful for converting the fluorescent radiation into form usable for detection. Preferably, the fluorescent radiation detection means 88 comprises a photodiode (not shown) which converts the electromagnetic radiation into an electrical signal. Alternatively, the fluorescent radiation detection means 88 may comprise an amplifier (not shown) which increases the intensity of the fluorescent radiation to a level that may be visually detected. In another embodiment, sufficient fluorescent material may be used that the concentration of fluorescent material in the surrounding medium is high enough to produce visible light without amplification.

If the fluorescent radiation detection means 88 comprises a photodiode or similar device which converts the fluorescent radiation into an electrical signal, then the electrical signal thus created is transmitted to a display means 92. The display means may be as simple as an LED which emits light when a current is applied. Alternatively, the display means 92 may comprise an analog meter. In another alternative, the display means 92 may comprise a processor which converts the signal to a digital quantity able to be displayed on an LCD display, for example. In yet another embodiment, especially where the electromagnetic radiation source 82 and fluorescent radiation detection means 88 are installed on the exterior of the equipment tank or switch compartment, the display means 92 comprises a transmitter which transmits the detected information by low voltage electrical connection, radio frequency or other methods to a remote observation site (not shown). Additionally, it is noted that in certain embodiments a display means is not necessary.

Figure 9:
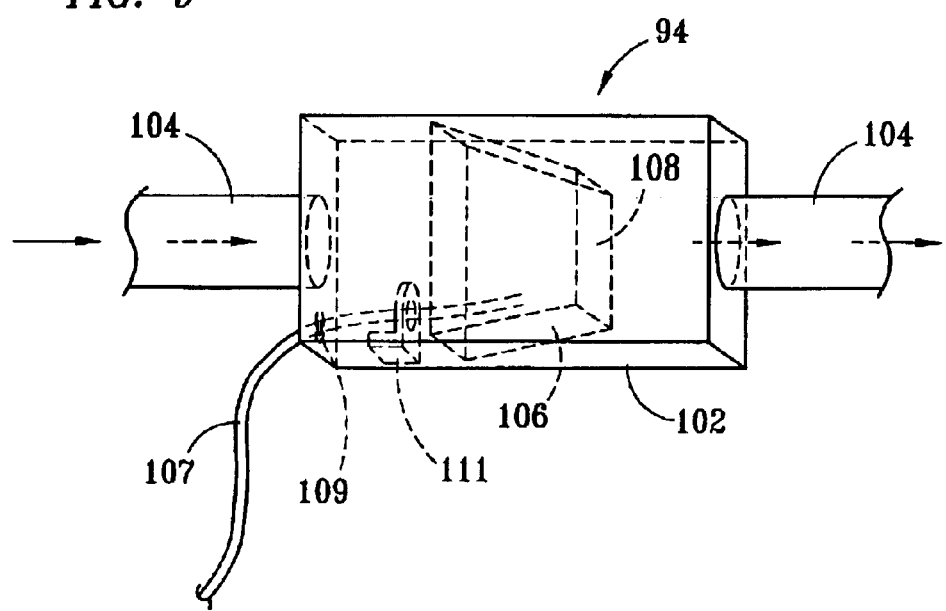
FIG. 9 is a perspective view of a particulate concentration or collection device employed in connection with monitoring for or detecting trace material.

Shown in FIG. 9 is a particulate concentration device 94 that may be used to aid in the detection of fluorescent trace material in the surrounding medium. The particulate concentration device 94 is configured for use in equipment having a forced-circulation system for filtering the oil surrounding the contacts. The particulate concentration device 94 is preferably located on a conduit which directs the flow of oil through the circulation system. A filter bed 106, constructed from a filtering material, substantially covers the area of oil flow through the particulate concentration device 94. The filter bed is preferably tapered in the direction of oil flow and preferably terminates at a collection surface 108.

As oil circulates through the particulate concentration device 94, some of the fluorescence trace material present in the oil, if any, will collect on the collection surface 108. In this embodiment, an optical transmission conduit 107 serves as the electromagnetic radiation transmission means 84 and the fluorescent radiation transmission means 86. The optical transmission conduit 107 extends through a wall of the particulate concentration device 94 to a position near the collection surface 108. A fitting 109 is provided in the wall of the particulate concentration device 94 to provide a seal around the optical transmission conduit 107. An end of the optical transmission conduit 107 is held in place by a first brace 111. Alternatively, a particulate concentration device 94 may be utilized with any trace material, not only a fluorescent trace material.

Electromagnetic radiation from the electromagnetic radiation source 82 is directed to the collection surface 108. Some of the fluorescent radiation produced by the fluorescent trace material on the collection surface 108 is directed through the fluorescent radiation transmission means 86 to a fluorescent radiation detection means 88.

Figure 10:
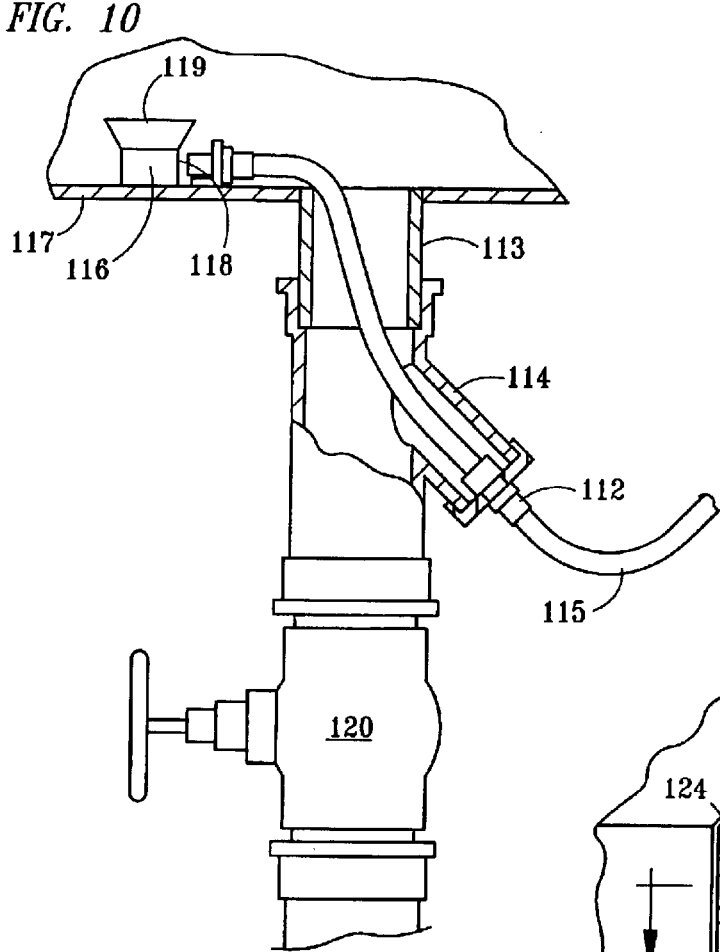
FIG. 10 is a side view, in partial section, of a drain assembly of a tank or switch compartment including an optically-transmissive conduit and port employed to monitor or detect trace material.

Shown in FIG. 10 is a particulate collection reservoir 116, which may be used in a tank or switch compartment as an alternative to the particulate concentration device 94 of FIG. 9, especially in a tank or switch compartment which does not include a forced-circulation filtration system. The particulate collection reservoir 116 is preferably located on a floor 117 of the tank or switch compartment, at a point at which fluorescent trace material is likely to settle after being released from a cavity in a contact assembly or baffle plate, for example. A particulate collection funnel 119 is preferably positioned over the particulate collection reservoir 116 to aid in the collection of the trace material, however, the particulate collection funnel 119 may alternatively be omitted.

Again in this embodiment, an optical transmission conduit 115 serves as an electromagnetic radiation transmission means 84 and a fluorescent radiation transmission means 86. The optical transmission conduit enters the tank or switch compartment through a port 112, provided in a portion of a drain pipe 113, having an access opening 114. The access opening 114 is preferably nearer to the tank or switch compartment than a drain valve 120.

The end of the optical transmission conduit 115 is preferably positioned so that electromagnetic radiation from the electromagnetic radiation source 82 is directed towards a translucent or transparent observation wall 118 of the particulate collection reservoir 116. Any fluorescent trace material within the particulate collection reservoir 116 is excited by the electromagnetic radiation. A portion of the resulting fluorescent radiation, if any, is transmitted through the fluorescent radiation transmission means 86 to a fluorescent radiation detection means 88.

Figure 11A:
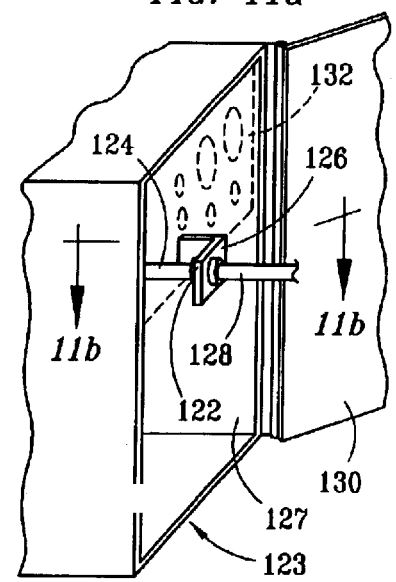
FIG. 11a is a perspective view of a remote optical access port within an equipment control cabinet.
Figure 11B:
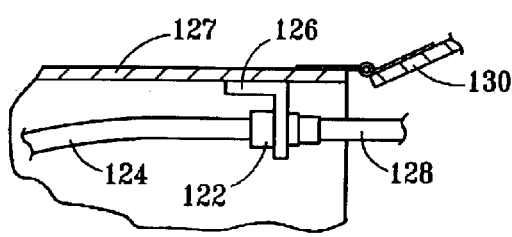
Figure 11C:
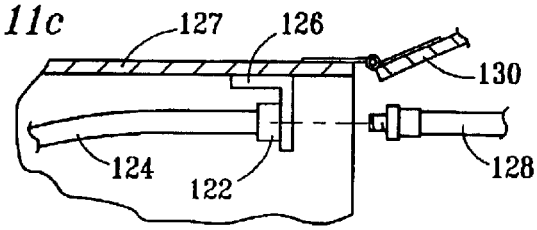
FIG. 11c is a top view, in partial section, of the remote optical access port of FIG. 11b, with a detached mobile transmission cable.

FIGS. 11a, 11b and 11c illustrate a remote access port 122 through which an electromagnetic radiation source 82 and a fluorescent radiation detection means 88 may access the oil or other medium surrounding a switch. Preferably, one end of a permanent transmission cable 124 is connected to the remote access port 122, while an opposite end (not shown) is positioned at an appropriate place in the tank or switch compartment. The remote access port may be used in conjunction with the embodiments shown in either FIG. 9 or 10, or other embodiments.

The remote access port 122 is preferably mounted on a wall 127 of an equipment control cabinet 123, to allow for easy access by an operator. In FIG. 11a a generic instrument panel 132 is shown in broken lines to aid in interpretation of the figure. The remote access port 122 is preferably held in place by a second brace 126. Alternatively, the remote access port 122 may be mounted to an existing instrument panel, such as generic instrument panel 132, for example. When not in use, the remote access port 122 is preferably enclosed behind a door 130 to the equipment control cabinet.

The remote access port 122 is configured to engage an end of a mobile transmission cable 128 and to allow transmission of electromagnetic radiation from the mobile transmission cable 128 to the permanent transmission cable 124 and vice versa. The end of the mobile transmission cable 128 is preferably configured for easy installation into and removal from the remote access port 122. In this embodiment, the mobile transmission cable 128 and permanent transmission cable 124 serve as an electromagnetic radiation transmission means 84 and a fluorescent radiation transmission means 86.

Having thus described the present invention by reference to certain of its preferred embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Many such variations and modifications may be considered obvious and desirable by those skilled in the art based upon a review of the foregoing description of preferred embodiments. Many other forms of switches and other electrical contacts are known in the art and could be used in conjunction with features of the invention. Accordingly, it is appropriate that the appended claims be construed broadly and in a manner consistent with the scope of the invention.

What is claimed is:

1. A method for determining erosion of a contact assembly, the method comprising:

providing a fluorescent trace material within the contact assembly;

allowing the contact assembly to be eroded until at least a portion of the fluorescent trace material is released into a surrounding medium;

circulating the surrounding medium through a particulate concentration device;

directing electromagnetic radiation onto the fluorescent trace material in the particulate concentration device; and detecting the fluorescent radiation emitted in response to the electromagnetic radiation.

2. The method of claim 1, wherein:

the particulate concentration device comprises a transparent or translucent observation wall; and the electromagnetic radiation is directed through the observation wall to the fluorescent trace material.

3. A method for determining the level of a fluorescent trace material present in a medium surrounding an electrical contact assembly, comprising the steps of:
   circulating the surrounding medium through a particulate concentration device containing a collection surface;
   directing electromagnetic radiation to the particulate concentration device; and
   detecting the fluorescent radiation generated by the fluorescent trace material collected by the particulate concentration device in response to the electromagnetic radiation.

4. A method for determining erosion of a contact assembly, the method comprising:
   providing a fluorescent trace material within the contact assembly;
   allowing the contact assembly to be eroded until at least a portion of the fluorescent trace material is released into a surrounding medium;
   directing electromagnetic radiation onto the fluorescent trace material in a the particulate concentration device; and
   detecting the fluorescent radiation emitted in response to the electromagnetic radiation.

* * * * *